(12) United States Patent
Kaigler, Sr.

(10) Patent No.: US 11,179,298 B2
(45) Date of Patent: *Nov. 23, 2021

(54) IMPLANT PELLETS AND METHODS FOR PERFORMING BONE AUGMENTATION AND PRESERVATION

(71) Applicant: Innovative Health Technologies, LLC, Anchorage, AK (US)

(72) Inventor: Darnell Kaigler, Sr., Detroit, MI (US)

(73) Assignee: INNOVATIVE HEALTH TECHNOLOGIES, LLC, Anchorage, AK (US)

(*) Notice: Subject to any disclaimer, the term of this patent is extended or adjusted under 35 U.S.C. 154(b) by 560 days.

This patent is subject to a terminal disclaimer.

(21) Appl. No.: 15/785,077

(22) Filed: Oct. 16, 2017

(65) Prior Publication Data

US 2019/0110868 A1 Apr. 18, 2019
US 2020/0237482 A9 Jul. 30, 2020

Related U.S. Application Data

(60) Continuation of application No. 15/090,201, filed on Apr. 4, 2016, now Pat. No. 9,814,544, which is a continuation of application No. 13/362,807, filed on Jan. 31, 2012, now Pat. No. 9,301,816, which is a division of application No. 12/350,754, filed on Jan. 8, 2009, now Pat. No. 8,128,706.

(60) Provisional application No. 61/006,372, filed on Jan. 9, 2008.

(51) Int. Cl.
*A61K 6/891* (2020.01)
*A61K 6/80* (2020.01)
*A61K 6/802* (2020.01)
*A61C 8/02* (2006.01)

(52) U.S. Cl.
CPC ............ *A61K 6/891* (2020.01); *A61C 8/0006* (2013.01); *A61K 6/80* (2020.01); *A61K 6/802* (2020.01)

(58) Field of Classification Search
None
See application file for complete search history.

(56) References Cited

U.S. PATENT DOCUMENTS

| | | | |
|---|---|---|---|
| 6,869,445 B1* | 3/2005 | Johnson | A61L 27/10 623/17.11 |
| 8,128,706 B2* | 3/2012 | Kaigler, Sr. | A61C 8/0016 623/23.57 |
| 9,814,544 B2* | 11/2017 | Kaigler | A61C 8/0006 |
| 2004/0043052 A1* | 3/2004 | Hunter | A61L 29/085 424/426 |
| 2006/0136071 A1* | 6/2006 | Maspero | A61L 27/56 623/23.76 |
| 2007/0196230 A1* | 8/2007 | Hamman | A61K 35/12 419/2 |

* cited by examiner

*Primary Examiner* — Carlos A Azpuru
*Assistant Examiner* — Casey S Hagopian
(74) *Attorney, Agent, or Firm* — Haynes and Boone, LLP

(57) ABSTRACT

Embodiments described herein are related to pellets that are placed within an extraction site that is in need of bone augmentation and preservation. The pellets are typically cylindrical in shape and comprise a material and a polymer coating. The goal of the pellets are to encourage sufficient new bone growth that jaw bone deterioration is prevented. The pellets create, arrange, and assemble an ideal growth environment for new bone growth to rapidly grow and preserve the original contours of an individual's jaw bone.

13 Claims, 3 Drawing Sheets

IMPLANT PELLETS AND METHODS FOR PERFORMING BONE AUGMENTATION AND PRESERVATION

CROSS REFERENCE TO RELATED APPLICATIONS

This application is a continuation of U.S. patent application Ser. No. 15/090,201, filed Apr. 4, 2016 (now allowed), which is a continuation of U.S. Pat. No. 9,301,816, issued Apr. 5, 2016, which is a division of U.S. Pat. No. 8,128,706, issued Mar. 6, 2012, which claims priority from U.S. Provisional Application No. 60/006,372, filed Jan. 9, 2008, the entire contents of each of which is hereby incorporated herein by express reference thereto.

FIELD OF THE INVENTION

Embodiments described herein relate generally to apparatuses and methods for dental surgery, and particularly to apparatuses and methods for performing bone preservation and/or augmentation.

BACKGROUND OF THE INVENTION

When an extracted or otherwise missing tooth is not immediately grafted or replaced with an implant, atrophy of the alveolar bone or jaw bone occurs over time. Consequently, individuals who have been partially edentulous for an extended period of time are left with an atrophic alveolar ridge that cannot securely support a denture. Furthermore, the edentulous individual faces deteriorated aesthetics and a compromised ability to chew and must be rehabilitated leaving the quality of the individual's oral health in an unfortunate state.

The buccal and lingual portions of the alveolar bone are composed of soft trabecular bone which has the unique characteristic of being capable of absorbing the shocks caused by the movement of teeth during speech, eating, etc. The removal of a tooth and the resulting absence of the bone pressure stimuli in the area causes the alveolar bone to resorb in that area. The result can be loss of 40-60% of the alveolar ridge's former height. After this initial 40-60% loss, the alveolar bone can continue to resorb at a bone loss rate of 0.5-1.0% per year.

In addition, when teeth are extracted, the lack of supporting bone fails to sufficiently support the load of a later inserted prosthesis or implant. This is a byproduct of the alveolar bone becoming weaker due to the lack of internal stimulation leading to a softer, porous, less dense, and spongier nature of the deteriorated bone. In addition, dental implants are prone to fail due to the porous nature of the bone and a lack of bone density.

Improved materials and techniques for augmenting, preserving and supporting bone growth are needed to decrease alveolar ridge deterioration and enhance the alveolar bone support of an oral prosthesis or implant.

BRIEF SUMMARY OF THE INVENTION

Embodiments described herein include a device called a pellet that is either placed within a fresh extraction site of the gum or onlayed on existing bone tissue. The pellet is designed to facilitate bone formation (preservation or augmentation) within the tooth socket. The pellet can be of various lengths, widths and shapes depending on the jaw bone deficiency. The pellet comprises one or more biocompatible materials having a polymer coating or a combination composite coating consisting of polymers and other biomaterials (degradable or nondegradable). The one or more biocompatible materials are arranged or assembled into a solid, matrix or mesh-like structure designed to enhance a bone growth environment by osteoinduction or osteoconduction. After insertion, the pellet facilitates new bone growth formation for preservation and/or augmentation. Over time, an integrated bone tissue, which is the obtained integration between the growing bone and the pellet, develops. Once adequate bone growth has occurred, the integrated bone structure can support a prosthesis or can be cored to create an opening, which can accommodate an implant device. Thus, the resulting foundation can provide enhanced support, fixation, and anchoring strength for a prosthesis or implant device due to the preservation and/or augmentation of the bone tissue.

DETAILED DESCRIPTION OF THE INVENTION

Figure 1A:
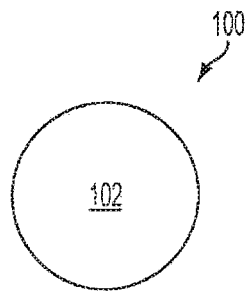
FIG. 1A illustrates a cross-sectional portion of a pellet in accordance with a first embodiment discussed herein.

Embodiments discussed herein provide techniques and pellets for preserving and augmenting bone growth particularly well suited for decreasing alveolar ridge deterioration and enhancing support of a prosthesis. In the following description, numerous specific details are set forth, such as material types, dimensions, specific tissues, etc., in order to provide a thorough understanding of the present invention. Practitioners having ordinary skill in the biomedical arts will understand that the invention may be practiced without many of these details. In other instances, well-known devices, methods, and biochemical processes have not been described in detail to avoid obscuring the claimed invention.

As described above, one problem associated with the failure of a prosthesis is the inability of the surrounding bone to support the load of the implant. This is especially true in areas that are weaker due to the softer, porous, less dense, or spongier nature of the alveolar bone or jaw bone. In particular, dental implants are prone to fail due to lateral, anterior or posterior movement of the prosthesis together with lack of a rigid surrounding bone structure. This problem similarly affects the stabilization of a tooth implant or prosthesis.

Another problem with the failure of a prosthesis is due to a deteriorating jaw bone. When an extracted or otherwise missing tooth is not immediately grafted or replaced with an implant, atrophy of the jaw bone occurs over time resulting in compromise esthetics and compromised ability to function.

Embodiments discussed herein offer solutions to the foregoing problems by providing pellets that can be placed into a cavity of bone to enhance the structural integrity, reduce bone deterioration, and protect the original (pre-extraction) shape of the bone itself. According to one embodiment, a pellet comprises a material arranged in a structured, matrix manner. After inserting the pellet into a cavity of bone, natural infiltration occurs as a result of and facilitated by the pellet's insertion such that new bone growth fills the internal cavity and replaces biodegradable portions of the pellet. Alternatively, the bone growth may fill internal pores of the pellet formed by the matrix nature of the pellet. The material comprising the pellet functions as an ideal growing environment for newly formed bone. By using means such as the pellet, new bone growth will occur (at an accelerated pace if seeded or grow at a normal pace if unseeded), as explained in greater detail below. The new bone growth can be used to support a prosthesis or denture with enhanced stability compared to a prosthesis or implant without such bone growth.

Optionally, the resulting integrated bone structure of the pellet can be cored or otherwise shaped to create an opening to accommodate an implant device. The pellet typically has a cylindrical lateral cross sectional shape but may take on any shape that facilitates bone augmentation and/or preservation depending on the jaw bone or skeletal deficiency. For example, in addition to cylindrical, the shape of the pellet may have a cross-sectional shape that is elliptical, rectilinear, round, etc. The shape of the pellet can also be tailored to fit the exact dimensions of the cavity. It should be appreciated that the precise shape of the pellet should not be limited to examples described above. The shape of the pellet, however, is usually slightly smaller in diameter than the receptor site or the site of extraction. It should be noted that where the site of extraction is smaller than the pellet, surgery may be needed to increase the size of the receptor site. Optionally, surgery may be required to "clean" the site (e.g., removal of extra tissue and/or bone fragments, etc.). Optionally, the pellet can be specifically designed for simple insertion into the receptor site. For example, careful measurements of the receptor site can be taken, and the pellet can be created for the particular receptor site. Measurements such as, for example, "casts" can be taken as known in the art. The purpose of the pellet is to preserve bone tissue and facilitate new bone growth such that jaw bone deterioration is prevented. Another purpose is to minimize the loss of bone volume. These goals are achieved by placing the pellet into the defect, and creating, arranging, or assembling an ideal growth environment to facilitate new bone growth and preserve the original contours of an individual's jaw bone tissue. The arrangement of the materials within the pellet may be entirely random or may consist of a fabric-like pattern having a more regular, organized blueprint. For example, conventional 3D printing manufacturing methods (described below) can be used to create fabric-like patterns and are considered acceptable for producing the pellet of the present invention.

Figure 1B:
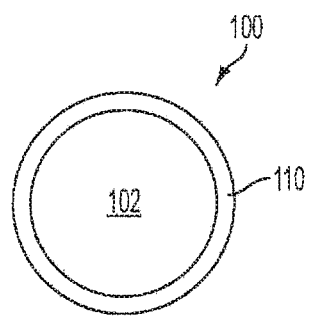
FIG. 1B illustrates a cross-sectional portion of the pellet in accordance with a second embodiment discussed herein.

With reference to FIGS. 1A-1B where like elements are designated by like numerals, various steps in the preparation of the material utilized, in accordance with one embodiment of the invention, to form the pellet are illustrated. FIG. 1A shows a portion of the pellet 100 that comprises a material 102. The material 102 is a degradable or non-degradable bioceramic material, e.g., hydroxyapatite, reinforced polyethylene composite, betatricalciumphosphate, substituted calcium phosphates, bioactive glass, resorbable calcium phosphate, alumina, zirconia, etc. that may be manufactured in a solid or mesh-like (described below) structure. It should also be noted that a biodegradable polymer can be used in combination with the bioceramic material to form a composite material to use as material 102. In the preferred embodiment, a hydroxyapatite material is utilized as the material 102 to form the pellet 100. It should be appreciated that the material 102 forming pellet 100 can be any type of material known in the art having characteristics that result in non-toxic byproducts.

For example, pellet 100 can be formed of synthetic polymers (alone or in combination) such as polyurethanes, polyorthoesters, polyvinyl alcohol, polyamides, polycarbonates, poly(ethylene) glycol, polylactic acid, polyglycolic acid, polycaprolactone, polyvinyl pyrrolidone, marine adhesive proteins, and cyanoacrylates, or analogs, mixtures, combinations, and derivatives of the above. Pellet 100 can also be formed of naturally occurring polymers or natively derived polymers (alone or in combination) such as agarose, alginate, fibrin, fibrinogen, fibronectin, collagen, gelatin, hyaluronic acid, and other suitable polymers and biopolymers, or analogs, mixtures, combinations, and derivatives of the above. Also, pellet 100 can be formed from a mixture of naturally occurring biopolymers and synthetic polymers. Alternatively, pellet 100 can be formed of a collagen gel, a polyvinyl alcohol sponge, a poly(D,L-lactide-co-glycolide) fiber matrix, a polyglactin fiber, a calcium alginate gel, a polyglycolic acid mesh, polyester (e.g., poly-(L-lactic acid) or a polyanhydride), a polysaccharide (e.g., alginate), polyphosphazene, or polyacrylate, or a polyethylene oxide-polypropylene glycol block copolymer. Pellet 100 can be produced from proteins (e.g. extracellular matrix proteins such as fibrin, collagen, and fibronectin), polymers (e.g., polyvinylpyrrolidone), or hyaluronic acid. Synthetic polymers can also be used, including bioerodible polymers (e.g., poly(lactide), poly(glycolic acid), poly(lactide-co-glycolide), poly(caprolactone), polycarbonates, polyamides, polyanhydrides, polyamino acids, polyortho esters, polyacetals, polycyanoacrylates), degradable polyurethanes, non-erodible polymers (e.g., polyacrylates, ethylene-vinyl acetate polymers and other acyl substituted cellulose acetates and derivatives thereof), non-erodible polyurethanes, polystyrenes, polyvinyl chloride, polyvinyl fluoride, poly(vinylimidazole), chlorosulphonated polyolifins, polyethylene oxide, polyvinyl alcohol, Teflon®, and nylon.

Bioceramics employed as material 102 within the pellet 100 can fall into all three biomaterial classifications, i.e., inert, resorbable and active, meaning they can either remain unchanged, dissolve or actively take part in physiological processes. There are several calcium phosphate ceramics that are considered biocompatible and possible materials for the pellet 100. Of these, most are resorbable and will dissolve when exposed to physiological environments, e.g., the extracellular matrix. Some of these materials include, in order of solubility: Tetracalcium Phosphate ($Ca_4P_2O_9$) >Amorphous calcium Phosphate >alpha-Tricalcium Phosphate ($Ca_3(PO_4)_2$)>beta-Tricalcium Phosphate ($Ca_3(PO_4)2$) >>Hydroxyapatite ($Ca_{10}(PO_4)_6(OH)_2$). Unlike the other certain calcium phosphates listed above, hydroxyapatite does not break down under physiological conditions. In fact, it is thermodynamically stable at physiological pH and actively takes part in bone bonding, forming strong chemical bonds with surrounding bone. This property is advantageous for rapid bone repair after surgery. Other bioceramic materials such as Alumina and Zirconia are known for their general chemical inertness and hardness. These properties can be exploited for implant device support purposes, where it is used as an articulating surface for implant devices. Porous alumina can also be used as a bone spacer, where sections of bone have had to be removed due to various conditions or diseases. The material acts as a scaffold or matrix for bone growth.

FIG. 1B illustrates a cross-sectional portion of the pellet 100 having a reinforced polymer and/or composite coating 110 that covers material 102 of the pellet 100. For example, when pellet 100 comprises a bioceramic material, polymer coating 110 comprises a polyactic acid or other hydrogel, which may be formed according to ordinary methods. It should be appreciated that polymer coating 110 does not have to be a complete polymer material, e.g., 100% polymer, but can be a composite material comprising a combination of any known bioceramic materials, composite hydrogels, and polymers. Moreover, the polymer coating can be made from a membrane such as collagen felt, or a similarly semi-rigid material, such as polylatic acid, polyether, etc. In the preferred embodiment, polymer coating 110 is a bio-resorbable polymer. The preferred bio-resorbable polymer exhibits characteristics such as favorable handling properties that make the polymer easy to use (i.e., requires no additional training for the operator to learn how to use, long-term, indefinite shelf life, economical, does not add considerable cost to patients, conforms to the receptor site, highly biocompatible and partially biodegradable, low cost to manufacturer, biomimetic after placement, easy to distribute, space maintenance (maintains shape of bone), supports cell growth and differentiation, chemotaxic properties (recruits wound healing host cells from surrounding tissue), and osteoconductive and osteoinductive). In addition, the polymer coating serves the purpose of preventing contamination of material 102 while safe guarding, and not altering, the environment of an individual's mouth. The polymer coating 110 may be infused onto material 102 as a liquid or viscous gel substance.

Pellet 100 can also comprise an additional bone morphogenic protein (BMP) material by incorporating the BMP into material 102. The additional protein serves as a stimulus for bone growth, in other words, an additional mechanism by which the present invention promotes accelerated bone growth within the pellet 100. The BMPs induce new bone growth within the pellet through a process resembling endochondral bone formation. In one embodiment, the BMP material comprises a protein substance and is mixed into material 102 forming a composite pellet material. The material 102 also can be infused with a collagen bone morphogenic protein base. It should be appreciated that the protein material may also comprise other growth proteins. Fibrinogen, a-thrombin, as well as other various antibiotics, growth hormones, gene therapies, or combinations of these factors may also be utilized in the material 102 to promote healthy bone growth. The BMP material may be infused within material 102 as a liquid or viscous gel substance.

Figure 2:
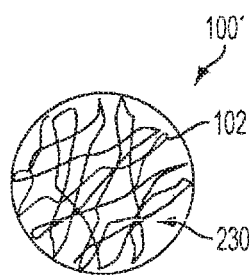
FIG. 2 illustrates a cross-sectional portion of the pellet in accordance with a third embodiment discussed herein.

It should be noted that pellet 100' may comprise a material 102, as shown in FIG. 2, having a mesh-like structure 230. The material 102 can be constructed in a woven, mesh-like manner that allows the new bone growth to grow throughout the structure to form pellet 100'. The mesh-like structure 230, in comparison to a solid structure, provides a greater amount of exposed surface area for bone growth to occur. The mesh-like structure 230 has a porous nature; and its pores can be substantially uniform or non-uniform. The mesh-like structure 230 of pellet 100' serves as a scaffold for the new bone growth. The pores can be vertically arranged or horizontally arranged; the pores can be arranged in an organized fashion or randomly sized and arranged according to the desires of the user.

At times, biodegradable polymers suffer from warping, hollowing or substantial erosion inherent with the process of degradation. In order to manage such a problem, polymers with high crystallinity are utilized. Self-reinforced and ultra-high strength bioabsorbable composites are readily assembled from partially crystalline bioabsorbable polymers, like polyglycolides, polylactides and glycolide/lactide copolymers. These materials have high initial strength, appropriate modulus and strength retention time from 4 weeks up to 1 year in-vivo, depending on the implant geometry. Reinforcing elements such as fibers of crystalline polymers, fibers of carbon in polymeric resins, and particulate fillers, e.g., hydroxyapatite, may also be used to improve the dimensional stability and mechanical properties of biodegradable devices. The use of interpenetrating networks (IPN) in biodegradable material construction has been demonstrated as a means to improve mechanical strength. To further improve the mechanical properties of IPN-reinforced biodegradable materials, biodegradable plates may be prepared as semi-interpenetrating networks (SIPN) of cross-linked polypropylene fumarate within a host matrix of poly(lactide-co-glycolide) 85:15 (PLGA) or poly(l-lactide-co-d,l-lactide) 70:30 (PLA) using different crosslinking agents.

Resin composites with incorporated polytetrafluoroethylene (PTFE) particles improve the hydrophobicity and surface properties of device implants, e.g., pellet 100. PTFE has high resistance to chemical regents, low surface energy, tolerance to low and high temperatures, resistance to weathering, low friction wiring, electrical insulation, and slipperiness. However, because conventional PTFE has poor resistance to abrasion, the inventor contemplates cross-linking PTFE with gamma-beam irradiation can be employed to drastically enhances resistance to abrasion and deformation. Further, the composites made of braided carbon fibers and epoxy resins (so called biocompatible carbon-epoxy resin) have better mechanical properties than composites made of short or laminated unidirectional fibers.

Figure 3:
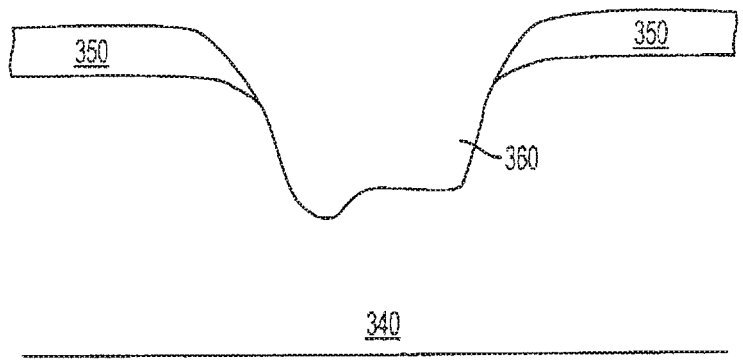
FIGS. 3-5 illustrate various stages of performing bone augmentation in accordance with an embodiment discussed herein.
Figure 4:
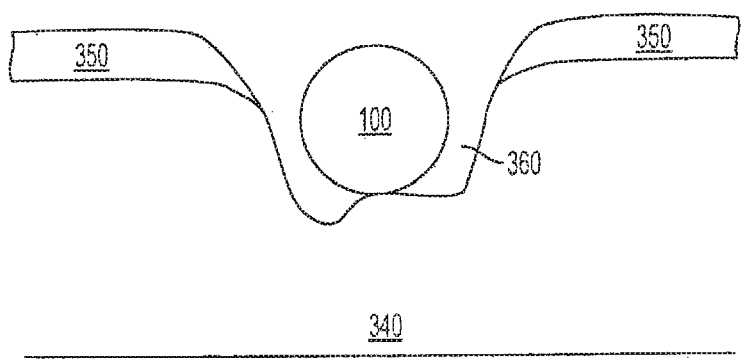
Figure 5:
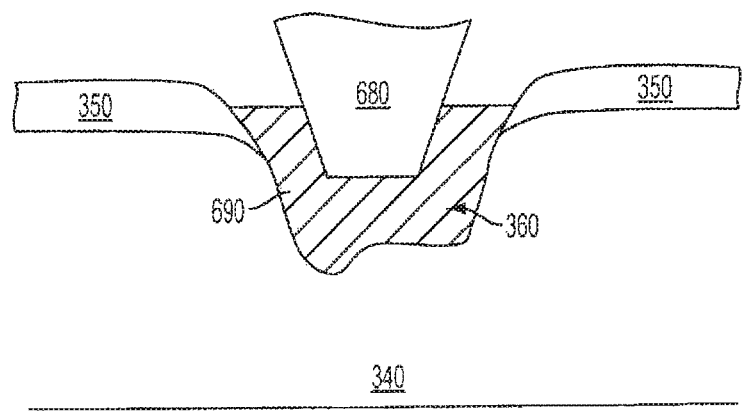

FIGS. 3-5 show various stages of one particular application of the pellet according to the present invention. By way of example, this sequence of drawings shows the implantation of a pellet into a receptor site, and the subsequent implantation of a dental implant into a newly grown jaw bone. The exemplar implant device comprises a dental implant of a type that is commonly used today, e.g., a titanium implant or a ceramic implant.

FIG. 3 shows a cross-section of bone 340 having an opening or cavity 360 surrounded by an epithelial tissue layer 350. In the case of a dental implant, cavity 360 may represent the space created by avulsion of the natural tooth previously occupying that space prior to extraction. In other applications, the cavity 360 may be created by the removal of either damaged or healthy bone in order to provide an attachment site for the implant device. Cavity 360 can also be created by the removal of cancerous tissue or tissue affected by any other type of disease capable of affecting the strength or shape of the tissue. Prior to inserting the pellet 100 into the cavity 360, the cavity 360 is cleaned and may be shaped utilizing conventional methods known in the art. As explained above, cavity 360 may be created by the removal of a natural tooth. In other instances, cavity 360 may result from the defect of a long bone created, for example, by dcbritement of a dysplasila. Cavity 360 can also result from any type of surgical procedure resulting in bone removal or any type of procedure that creates any type cavity.

FIG. 4 shows the cross-section of FIG. 3 following insertion of the pellet 100 into cavity 360. Pellet 100 may be shaped to conform to the size of the bone cavity 360. Once placed into cavity 360, the pellet remains secure within the cavity due to its polymer coating 110 (FIG. 1B). Polymer coating 110 (FIG. 1B) interacts with the blood surrounding cavity 360 forming a securing mechanism, e.g., a blood clot, that allows pellet 100 to stay in place without the use of a barrier membrane (not shown). Barrier membranes have been conventionally used to seal dental applications into a cavity such as cavity 360. The barrier layer formed by the polymer coating 110 prevents mucosal attachment or soft tissue growth which would inhibit bone growth. Instead, osteointegration of new bone growth to and within the pellet 100 is permitted to occur. It should be noted that the use of pellet 100 is exemplary and any of the embodiments of the pellet can be used.

Once bone growth into the cavity 360 is complete, the region can be used to support a prosthesis or may be cored or otherwise shaped to accept an implant device. FIG. 5 illustrates a bottom portion of an implant device 680 fixably secured/attached to bone 340 using the newly grown osteointegration bone 690. The osteointegrated bone 690, consisting of new bone, provides improved fixation for implant 680 over the previously existing deteriorated bone. Over time, it is expected that the bone 690 will further integrate onto the outer, submerged surface layer of implant 680.

It should be appreciated that additional applications of the embodiments of the invention exist for use in long bone or exo-augmentation. For example, this may involve the augmentation of bone onto the surface of existing skeletal bone. It is appreciated that the embodiments of the invention are also useful in the treatment of a fractured or shattered bone. The pellet material allows for bone integration at the damaged site as well as soft-tissue attachment to the surrounding soft tissue. It is appreciated that the pellet may be shaped in a variety of sizes. That is, due to its semi-rigid nature, it may be molted or adapted to fit a particular application or circumstance.

The elastic bending moment capacity of un-fractured bone up to the onset of plastic deformation (i.e., when stress in outer layer reaches yield value) is about 320 Nm. Bending moment of 320 Nm induce about 0.5% strains in callus and 0.9% in composite plate. For comparison, the modulus of elasticity of typical metals used in osteosynthetic devices is about 5 to 10 times that of bone which is 17-24 GPa. Callus formation, ossification and bone union are hampered by the lack of strain in bone. Braided composites deployed in this art should therefore be just strong enough (up to 24 GPa with high stiffness to weight ratio) to promote the healing, but not so stiff as to hinder bone architecture.

As referenced above, three-dimensional printing, described in U.S. Pat. No. 5,204,055, is one method of creating complex geometries in medical devices. Three-dimensional printing is also described in U.S. Pat. No. 5,370,692. Three-dimensional printing has been proposed for creating a variety of three dimensional medical devices, pharmaceuticals and implants, however, the prior methods of creating a device did not relate to engineered microstructures. The biostructure of the embodiments of the invention may be manufactured by three-dimensional printing followed, in certain embodiments, by appropriate post-processing steps. Three-dimensional printing allows the manufacture of biostructures of great geometric internal and external complexity including recesses, undercuts, internal voids and other geometric features, which are difficult or impossible to create with conventional manufacturing processes. Three-dimensional printing also allows the creation of compositional variation within the biostructure that may not be achieved by conventional manufacturing processes.

In three-dimensional printing, a layer of powder is deposited such as by roller spreading. After the powder layer has been deposited, a binder liquid is deposited onto the powder layer in selected places so as to bind powder particles to each other and to already-solidified regions. The binder liquid may be dispensed in the form of successive discrete drops, a continuous jet, or other form.

Binding may occur either due to deposition of an additional solid substance by the binder liquid, or due to dissolution of the powder particles or of a substance mixed in with the powder particles by the binder liquid, followed by resolidification. Following the printing of the binder liquid onto a particular layer, another layer of powder is deposited and the process is repeated for successive layers until the desired three-dimensional pellet is created. Unbound powder supports bound regions until the biostructure is sufficiently dry, and then the unbound powder is removed. Another suitable method that could be used to deposit layers of powder is slurry deposition.

The liquid thus deposited in a given pass binds powder particles together so as to form in the powder bed a line of bound material that has dimensions of bound material in a cross-section perpendicular to the dispenser's direction of motion. This structure of bound powder particles may be referred to as a primitive. The cross-sectional dimension or line width of the primitive is related in part to the diameter of the drops if the liquid is dispensed by the dispenser in the form of discrete drops, or to the diameter of the jet if the liquid is deposited as a jet, and also is related to other variables such as the speed of motion of the printhead. The cross-sectional dimension of the primitive is useful in setting other parameters for printing.

For printing of multiple adjacent lines, the line-to-line spacing may be selected in relation to the width of the primitive printed line. Also typically the thickness of the deposited powder layer may be selected in relation to the dimension of the primitive printed line. Typical drop diameters may be in the tens of microns, or, for less-demanding applications, hundreds of microns. Typical primitive dimensions may be somewhat larger than the drop diameter.

Printing is also described by a quantity called the saturation parameter. Parameters which influence printing may include flow rate of binder liquid, drop size, drop-to-drop spacing, line-to-line spacing, layer thickness, powder packing fraction, etc., and may be summarized as a quantity called the saturation parameter. If printing is performed with discrete drops, each drop is associated with a unit volume of powder that may be considered to have the shape of a rectangular prism.

In printing the described pellet, the at least one direction in which the unbound powder is not surrounded by bound powder provides access by which unbound powder can be removed after completion of three-dimensional printing. After drying of the three-dimensional printing biostructure, removal of unbound particles may first be done by simple methods such as gentle shaking or brushing, and further removal of powder from the interior of macrostructures may be aided by the use of sonication in liquid or other convention techniques known in the art. Structures made by three-dimensional printing may include changes of direction, changes of cross-section, branchings, and the like.

There are also other possible ways of making the pellet. One such method involves double-printing, i.e., printing on a layer of powder, allowing the volatile part of the binder liquid to evaporate essentially completely, and printing more binder liquid onto the same place such that the binder substance which remains after the last printing is built up above the actual powder particles in the bed. The next layer of powder which is spread or deposited cannot occupy the region which is occupied by the built-up binder substance from the "puddle" formed by the repeat printing(s) at the same location. Eventually, when the binder material in the puddle decomposes and exits as gaseous decomposition products, the absence of particles in the region formerly occupied by the puddle yields a macrostructure of empty space. Yet another possible method of making the pellet involves the chemical change of the composition of the powder particles. A second binder fluid that is chemically reactive may be printed in the region of the macrochannel such that the pellet is formed after burnout of the binder substance and chemical reaction of the particles with the chemically reactive binder such that the reaction product is soluble such as in water. Then, material in the macrochannel region may be dissolved or leached out to leave an open macrochannel.

What is claimed is:

1. A pellet configured for bone augmentation and preservation, the pellet comprising:
    an inner material for causing bone growth in a desired area, the inner material having a mesh-like structure and comprising a bioceramic material and a biodegradable polymer, wherein the biodegradable polymer comprises a partially crystalline bioabsorbable polymer; and
    a polymer coating completely surrounding and covering the inner material, wherein the pellet is sized to fill the dimensions of a bone extraction site as one piece, and the polymer coating comprises a polymer and a bioceramic material.

2. The pellet of claim 1, wherein the bioceramic material of the inner material comprises calcium phosphate.

3. The pellet of claim 1, wherein the bioceramic material of the inner material comprises hydroxyapatite.

4. The pellet of claim 1, wherein the bioceramic material of the inner material comprises tricalcium phosphate.

5. The pellet of claim 1, wherein the biodegradable polymer further comprises reinforcing material to improve dimensional stability.

6. The pellet of claim 1, wherein the bioceramic material of the inner material comprises hydroxyapatite and the inner material further comprises poly-lactide-co-glycolide.

7. The pellet of claim 1, wherein the bioceramic material of the inner material comprises hydroxyapatite and the inner material further comprises polycaprolactone.

8. The pellet of claim 1, wherein the polymer coating further comprises a hydrogel, and one or more polymers.

9. A pellet for performing bone augmentation and preservation, the pellet comprising:
    an inner material adapted to cause bone growth in a desired area, the inner material having a mesh-like structure and comprising a bioceramic material and a biodegradable polymer, wherein the biodegradable polymer comprises a partially crystalline bioabsorbable polymer; and
    a polymer coating completely surrounding and covering the inner material, wherein the polymer coating comprises a polymer and a bioceramic material.

10. The pellet of claim 9, wherein the bioceramic material of the inner material comprises calcium phosphate, hydroxyapatite, or tricalcium phosphate.

11. A pellet adapted to preserve and augment bone, the pellet comprising:
    an inner material adapted to cause bone growth in a desired area, the inner material having a mesh-like structure and comprising a bioceramic material and a biodegradable polymer, wherein the biodegradable polymer comprises a partially crystalline bioabsorbable polymer; and
    a polymer coating completely surrounding and covering the inner material, wherein the polymer coating comprises a bioceramic material, a hydrogel, and a polymer.

12. The pellet of claim 11, wherein the bioceramic material of the inner material comprises calcium phosphate, hydroxyapatite, or tricalcium phosphate.

13. The pellet of claim 11, wherein the biodegradable polymer further comprises a reinforcing material to improve dimensional stability.

* * * * *